United States Patent [19]
Kotliar

[11] Patent Number: 5,924,419
[45] Date of Patent: Jul. 20, 1999

[54] APPARATUS FOR PASSIVE HYPOXIC TRAINING AND THERAPY

[76] Inventor: Igor K. Kotliar, 50 Lexington Ave., Ste 249, New York, N.Y. 10010

[21] Appl. No.: 08/797,242

[22] Filed: Feb. 8, 1997

Related U.S. Application Data

[63] Continuation-in-part of application No. 08/739,379, Oct. 29, 1996, which is a continuation-in-part of application No. 08/505,621, Jul. 21, 1995, Pat. No. 5,799,652, which is a continuation-in-part of application No. 08/445,677, May 22, 1995.

[51] Int. Cl.$^6$ ............... A62B 7/00; A62B 23/02; A62B 31/00
[52] U.S. Cl. ............... 128/205.11; 128/205.12; 128/200.24; 128/205.26; 95/103
[58] Field of Search ............... 128/200.24, 202.12, 128/202.13, 205.11, 205.12, 205.26; 482/13; 55/338, 339; 95/45, 47, 51, 52, 138, 902, 103

[56] References Cited

U.S. PATENT DOCUMENTS

| | | | |
|---|---|---|---|
| 4,190,424 | 2/1980 | Armond et al. | 55/58 |
| 4,439,213 | 3/1984 | Frey et al. | 55/31 |
| 4,826,510 | 5/1989 | McCombs | 55/179 |
| 4,973,339 | 11/1990 | Bansal | 55/31 |
| 5,101,819 | 4/1992 | Lane | 128/204.18 |
| 5,346,536 | 9/1994 | Kaneshige et al. | 95/103 |
| 5,382,280 | 1/1995 | Choe et al. | 95/98 |
| 5,383,448 | 1/1995 | Tkatchouk et al. | 128/205.11 |

*Primary Examiner*—Kimberly L. Asher

[57] ABSTRACT

An apparatus for passive hypoxic training or therapy provides to a user hypoxic (low-oxygen) gas mixture having carbon dioxide content optimal for breathing stimulation and a comfortable humidity level. The apparatus reduces the oxygen content of the air by passing the ambient air through a pressure-swing adsorption separator which extracts the oxygen therefrom. The air pressurized by compressor is delivered in alternating sequence into cartridges having a molecular-sieve material which adsorbs nitrogen, carbon dioxide and water vapor and allows a dry oxygen-enriched fraction to pass through an to be discharged. Remaining hypoxic (low-oxygen) gas mixture is recovered by depressurization of cartridges and is delivered to a user through a surge tank, filter, breathing bag, and respiratory mask. To lower and regulate the oxygen content of the hypoxic gas mixture delivered for inhalation, part of it, collected in surge tank, can be added by a mixing regulator to the ambient air taken in by the compressor through the air intake filter.

4 Claims, 1 Drawing Sheet

APPARATUS FOR PASSIVE HYPOXIC TRAINING AND THERAPY

RELATED APPLICATION

This application is a CIP of Ser. No. 08/739,379 filed Oct. 29, 1996 (pending); which is a CIP of Ser. No. 08/505,621, filed Jul. 21, 1995 now U.S. Pat. No. 5,799,652; which is a CIP of Ser. No. 08/445,677 filed May 22, 1995 (pending).

FIELD OF THE INVENTION

The present invention relates to a process and equipment for providing a hypoxic environment to a user for hypoxic training in order to boost his/her immunity, increase physical strength, endurance and resistance to various deseases, and more particularly, to such a process and equipment which employs an oxygen-depleted gas mixture being delivered for inhalation by a user.

The benefits of hypoxic training and therapy are described in my previous applications and can be also found in the Hypoxia Medical Journal, Geneva-Moscow, and publications of the International Hypoxia Symposia held each year in different countries.

During inhalation of hypoxic air, the heart rate and breathing frequency increase and pulmonary ventilation is improved, In some countries, hypoxic training is used as a treatment for various diseases because it improves the patients immunity and resistance.

DESCRIPTION OF THE PRIOR ART

European patent EP 0472 799 AL and U.S. Pat. No. 5,207,623 and 5,383,448 show only one type of the apparatus for hypoxic therapy currently available on the market. The apparatus employs a membrane gas-separation principle and is heavy (100 kg) and noisy (80–100 dba.). The hypoxic gas mixture generated by membrane separation is absolutely dry and must be humidified.

But the main disadvantage of devices employing the membrane-separation principle is that the hypoxic air delivered to a user for inhalation is also free of carbon dioxide—a necessary breathing stimulant. Another significant disadvantage of these systems is the necessity of constant humidification of the produced gas mixture which requires frequent refilling of a humidifier bottle with distilled water (some users may not have it) and its sterilization.

Moreover, this apparatus is expensive (ca. $20,000), can produce only 15 L/min of a hypoxic gas mixture (which is not enough for hypoxic training of athletes), employs relatively high pressures for air separation (3–4 bar.), and requires a lot of energy (min. 0.4 kw). The poor supply of hypoxic air also makes its usage impossible for well-trained individuals and athletes having larger lung capacities.

SUMMARY OF THE INVENTION

A principal object of this invention is to provide an affordable apparatus for hypoxic training (hypoxicator) which requires less energy, produces more of the hypoxic gas mixture, and is smaller and lighter.

Another object of the present invention is to provide a system which produces a hypoxic gas mixture containing carbon dioxide in quantities most suitable for necessary breathing stimulation.

A further object of the present invention is to provide a system which supplies a user with an oxygen-depleted gas mixture containing a comfortable humidity level free of the necessity of artificial humidification with all its disadvantages.

Yet a further object of the invention is to provide a system which employs the pressure-swing adsorption principle to separate ambient air into an oxygen-enriched fraction being disposed outside of the system and a nitrogen-enriched fraction provided to a user for inhalation.

Among many advantages of the invented apparatus are: affordability, energy savings (it requires only 0.25 kw compressor), high productivity (up to 60 L/min. of hypoxic gas mixture), light weight (ca. 30 kg.), lower operating pressure (2 bar), and lower noise level (less than 50 dba @ 1 meter).

The main advantage is that the invented hypoxicator produces a hypoxic gas mixture of comfortable humidity containing carbon dioxide, which is necessary for breathing stimulation and considerably improves the benefits of hypoxic training and/or results of hypoxic therapy. The hypoxicator does not require special humidification means.

DESCRIPTION OF THE DRAWINGS

The sole FIGURE shows a schematic view of the most preferred embodiment.

DESCRIPTION OF THE INVENTION

Figure 1:
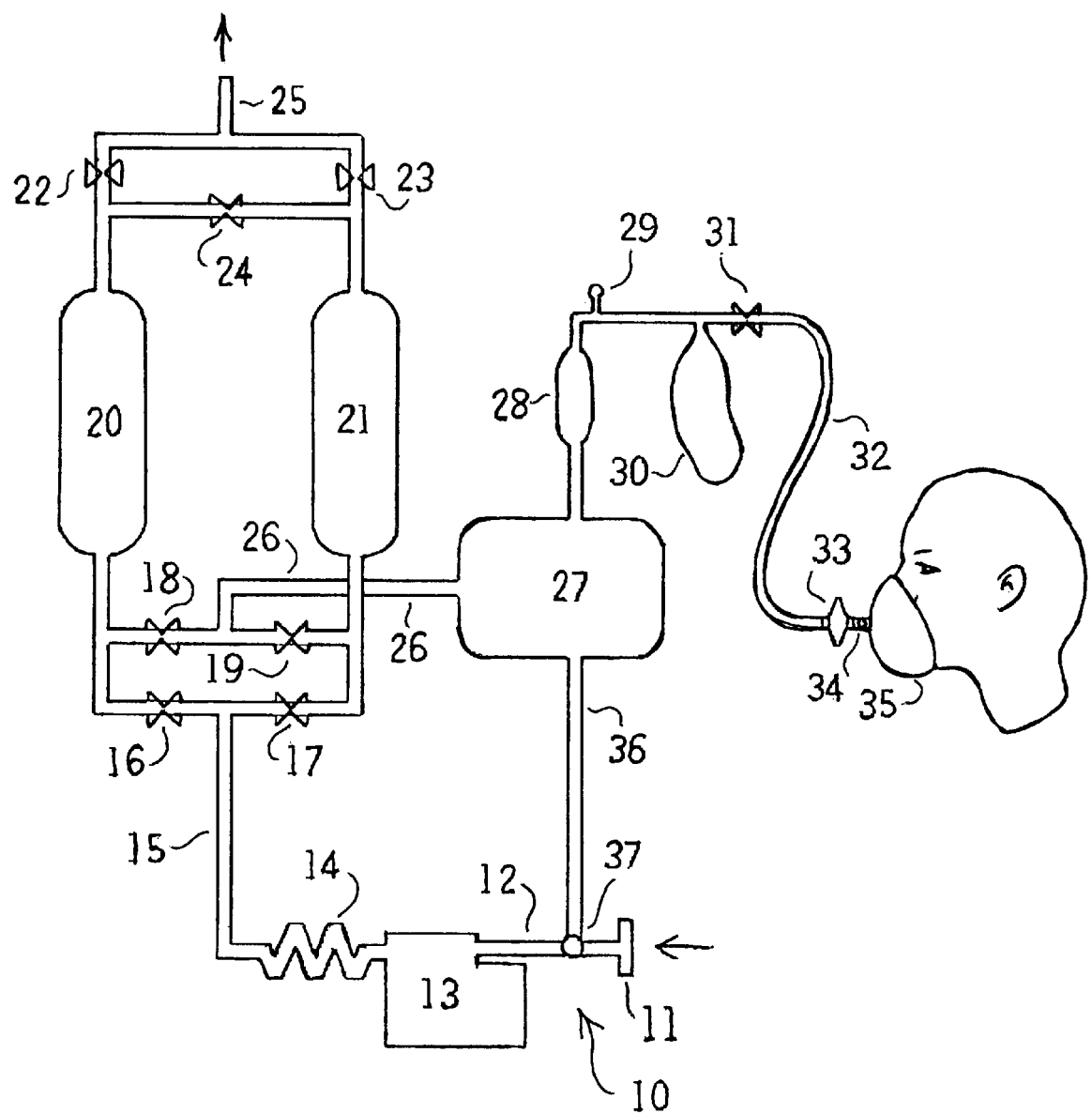

The basic object of this invention is to provide an apparatus for hypoxic training and therapy which provides hypoxic gas mixtures for inhalation containing carbon dioxide—a necessary breathing stimulant, and which does not require much maintenance and time-consuming daily preparations, such as cleaning and refilling of a humidifier bottle.

All this is possible because the apparatus presented here employs a pressure-swing adsorption principle which allows the removal of the dry, oxygen-enriched fraction from ambient air and to generate an oxygen-depleted gas mixture with increased humidity and carbon dioxide content in comparison to the ambient feed air.

The most preferred embodiment of the invented hypoxicator can produce up to 60 L/min of hypoxic air with a carbon dioxide content ranging usually from 500 ppm. to 1500 ppm., depending on the carbon dioxide content of the feed air and the desired oxygen content in the product. These slightly increased levels of carbon dioxide enhance stimulation of a user's respiratory system and produce far better results in hypoxic training and therapy. (It is a proven medical fact that carbon dioxide is a necessary breathing stimulant and is harmless in concentrations up to 3% or 30000 ppm.)

The invented hypoxicator can be used in medical facilities for hypoxic therapy and as a home-use device for passive hypoxic training of individuals, and specifically—athletes who require larger quantities of hypoxic air for breathing.

FIG. 1. shows a schematic view of the most preferred embodiment 10 of the invented hypoxicator which can be used for passive hypoxic training or therapy.

A compressor 13 draws ambient air through an intake filter 11 and conduit 12, and forces it into the system under 30 psi pressure. The pressurized air, being cooled in coil 14, is delivered through conduit 15 and valve 16 into cartridge 20, containing molecular sieve material, preferably zeolites, either synthetic or natural, or molecular sieve carbon, type CMSO2. While the molecular sieve material gradually becomes saturated with a nitrogen-enriched fraction, oxygen concentrate passes through valve 22 and is discharged into the atmosphere through outlet 25. At this time, valves 17, 18 and optional valve 24 are closed. Just before the molecular sieve material becomes saturated with nitrogen, valves 16, 19 and 22 close and valves 17, 18 and 23 open. The flow path of compressed air is redirected into cartridge 21, also containing the same molecular sieve material as cartridge 20. At the opening of valve 18, cartridge 20 undergoes depressurization, allowing the collected nitrogen to escape through conduit 26 into surge tank 27. The compressed air is then forced into cartridge 21, where the same process occurs as in cartridge 20, allowing oxygen to pass through valve 23 and to be discharged through outlet 25. A small amount of oxygen, being directed through the optional valve 24, can be used to purge the molecular sieve material of remaining nitrogen in cartridge 20.

Just before the molecular sieve material in cartridge 21 becomes saturated, valves 17, 18, and 23 close and valve 16, 19 and 22 open, allowing nitrogen collected in cartridge 21 to escape through valve 19 and conduit 26 into surge tank 27. Then, valve 24 opens briefly, allowing a small amount of oxygen concentrate into cartridge 21, purging the molecular sieve material of remaining nitrogen. The compressed air is again redirected through valve 16 into cartridge 20, continuing the alternating sequence. The number of pressurizing cartridges in the system may vary.

The oxygen-depleted (hypoxic) gas mixture having a larger humidity and carbon dioxide content than the ambient air is collected in surge tank 27. A HEPA (High Efficiency Particulate Arrestance) filter 28 is installed further in the flow path of the hypoxic gas mixture, which, passing an oxygen meter 29, is collected in an optional breathing bag 30. The HEPA filter 28 may be installed also after bag 30 and valve 31.

An oxygen analyzer 29 is installed in the hypoxic gas delivery line between tank 27 and filter 33 in order to control the oxygen content in the delivered gas mixture. The most preferable oxygen content for passive hypoxic training and therapy is 12% and may vary for some applications from 10% to 15%.

Suitable capsule HEPA filters are available from Gelman Sciences Inc. or Arbortech. Surge tank 27 may be made of metal, glass or plastic and can be even flexible. The breathing bag is preferably made of soft synthetic material (e.g. silicon rubber) and may be elastic.

The hypoxic gas mixture flows then from bag 30 through an optional low-pressure valve 31 into flexible delivery tubing 32 being connected to respiratory filter 33 and respiratory mask 35 having a back-flow valve 34 which prevents exhaled air from flowing back into the system.

The oxygen content in the delivered gas mixture may be regulated by redirecting a part of the hypoxic gas mixture from the surge tank 27 through the conduit 36 back into the air- intake conduit 12 which is achieved by installing a flow-mixing regulator 37. Regulator 37 allows the addition of some of the hypoxia gas mixture from the surge tank 27 to the ambient air taken in by compressor 13 through intake filter 11. The more hypoxic mixture is added to the ambient air taken in, the lower the oxygen content of the hypoxia gas mixture delivered for inhalation. Of course, this feature is optional and should be preferably employed for hypoxicators used under supervision in medical facilities.

In the most-preferred embodiment which employs a 0.248 kw WOB-L piston air compressor model 2750CGHI50 made by Thomas Industries Inc., the oxygen content in the delivered hypoxia gas mixture is 15% if 100% of the ambient air that is used has 20.9% O2. By recirculating part of the hypoxia air in the system, the oxygen content can be regulated by regulator 37 down to 10% or less.

The hypoxic air mixture provided by the most preferred embodiment 10 contains a comfortable humidity level, since water vapor is retained by the molecular sieve material and delivered to a user together with the hypoxic gas mixture. The carbon dioxide content of the delivered gas mixture can range from 500 to 1500 ppm, depending on the CO2 content in the ambient air and O2-content of the delivered gas mixture.

Molecular Sieve Carbon type MSN2 can also be used as an adsorption material in this system. However, it will adsorb oxygen, allowing nitrogen to pass through. In this case, outlet 25 is connected to surge tank 27, and conduit 26 is disconnected from surge tank 27. allowing collected oxygen to be discharged into the atmosphere. Temperature-swing adsorption process and other air-separation technologies can also be employed in this embodiment.

What is claimed is:

1. An apparatus for providing to a user reduced-oxygen air having moisture and carbon dioxide contents in quantities equal to or higher than that of ambient air, said apparatus comprising:

an oxygen-extraction system having an inlet taking in ambient air, and first and second outlets, said first outlet transmitting a first gas mixture having a higher oxygen content than the ambient air and said second outlet transmitting a second gas mixture having a lower oxygen content than the ambient air;

said oxygen-extraction system comprising a compressor and a pressure-swing absorption unit, said compresser drawing ambient air through said inlet and delivering said air under pressure to said pressure-swing adsorption unit said pressure-swing absorption unit having molecular sieve adsorption material therein for adsorbing nitrogen, carbon dioxide, and water vapor from the ambient air applied thereto and permitting passage of oxygen therethrough to be released from the apparatus into the atmosphere, said pressure-swing adsorption unit releasing said retained nitrogen, carbon dioxide and water vapor into said second gas mixture for transmission to said second outlet;

a delivery-line outlet communicating with said second outlet and receiving therefrom said second gas mixture;

said delivery-line outlet communicating with a hypoxic gas delivery line providing said second gas mixture for inhalation by a user.

2. The apparatus according to claim 1 and further comprising, a recirculation conduit, said gas delivery line having a recirculation-conduit outlet communicating through said recirculation conduit with said inlet taking in ambient air and delivering, when in use, part of said second gas mixture back into said oxygen-extraction system.

3. The apparatus according to claim 1 and further comprising, said hypoxic gas delivery line comprising a gas-delivery conduit installed with a HEPA-filter, an oxygen analyzer, a breathing bag, and a respiratory mask having a respiratory filter and a backflow preventive device.

4. The apparatus according to claim 1 and further comprising, said recirculation conduit having a gas mixing device for regulating flow of said second gas mixture being added to ambient air taken in.

* * * * *

UNITED STATES PATENT AND TRADEMARK OFFICE
CERTIFICATE OF CORRECTION

| | | Page 1 of 1 |
|---|---|---|
| PATENT NO. | : 5,924,419 | |
| APPLICATION NO. | : 08/797242 | |
| DATED | : July 20, 1999 | |
| INVENTOR(S) | : Igor K. Kotliar | |

It is certified that error appears in the above-identified patent and that said Letters Patent is hereby corrected as shown below:

The word "absorption" appearing in claim 1, lines 12 and 15 (col. 4, lines 31 and 34, respectively) should be changed to the word "adsorption" at both occurrences.

Signed and Sealed this
Eighth Day of November, 2011

David J. Kappos
*Director of the United States Patent and Trademark Office*